US 6,718,969 B1

(12) United States Patent
Rubin et al.

(10) Patent No.: US 6,718,969 B1
(45) Date of Patent: Apr. 13, 2004

(54) MEDICATION DOSAGE INHALER SYSTEM

(76) Inventors: Darren Rubin, 3844 Chaucer Way, Land O' Lakes, FL (US) 34639; Howard Rubin, 3844 Chaucer Way, Land O' Lakes, FL (US) 34639

( * ) Notice: Subject to any disclaimer, the term of this patent is extended or adjusted under 35 U.S.C. 154(b) by 108 days.

(21) Appl. No.: 10/156,206

(22) Filed: May 28, 2002

(51) Int. Cl.[7] .............................................. A61H 31/00
(52) U.S. Cl. ................................. 128/200.14; 482/13
(58) Field of Search .......................... 482/13; 600/532, 600/538, 539; 128/202.22, 204.23, 205.23, 204.11, 204.12, 200.14

(56) References Cited

U.S. PATENT DOCUMENTS

| | | | | |
|---|---|---|---|---|
| 3,079 A | * | 5/1843 | Rose ........................... | 482/13 |
| 369,849 A | * | 9/1887 | Werner ................... | 128/203.22 |
| 393,869 A | * | 12/1888 | Warren ................... | 128/203.24 |
| 515,637 A | * | 2/1894 | Wilhide ........................ | 482/13 |
| 576,041 A | * | 1/1897 | Denison ................ | 128/204.13 |
| 635,232 A | * | 10/1899 | Carroll ......................... | 482/13 |
| 737,008 A | * | 8/1903 | Nichol ......................... | 482/13 |
| 813,425 A | * | 2/1906 | Hill ........................ | 128/203.23 |
| 895,606 A | * | 8/1908 | Warde ......................... | 600/539 |
| 1,044,367 A | * | 11/1912 | Evans .................... | 128/202.21 |
| 3,298,362 A | * | 1/1967 | Lippitt et al. ................ | 600/481 |
| 3,863,914 A | * | 2/1975 | O'Connor .................... | 482/13 |
| 3,874,380 A | * | 4/1975 | Baum ..................... | 128/200.14 |
| 3,874,381 A | * | 4/1975 | Baum ..................... | 128/200.14 |
| 4,025,070 A | * | 5/1977 | McGill et al. ................. | 482/13 |
| 4,060,074 A | * | 11/1977 | Russo ................... | 128/200.18 |
| 4,062,358 A | * | 12/1977 | Kritzer ................... | 128/205.24 |
| 4,114,607 A | * | 9/1978 | Russo ........................ | 600/538 |
| 4,158,360 A | * | 6/1979 | Adams ........................ | 600/538 |
| 4,183,361 A | * | 1/1980 | Russo ........................ | 600/538 |
| 4,221,381 A | * | 9/1980 | Ericson ........................ | 482/13 |
| 4,253,468 A | * | 3/1981 | Lehmbeck .................. | 600/539 |
| 4,421,120 A | * | 12/1983 | Edwards et al. ............ | 600/538 |
| 4,444,202 A | * | 4/1984 | Rubin et al. ................. | 600/538 |
| 4,456,016 A | * | 6/1984 | Nowacki et al. ............ | 600/538 |
| 4,533,137 A | * | 8/1985 | Sonne ......................... | 482/13 |
| D280,765 S | * | 9/1985 | Alvino ....................... | D24/110 |
| 4,538,620 A | * | 9/1985 | Nowacki et al. ............ | 600/538 |
| 4,584,997 A | * | 4/1986 | Delong .................. | 128/205.23 |
| 4,601,465 A | * | 7/1986 | Roy ............................. | 482/13 |
| 4,671,269 A | * | 6/1987 | Wilp ...................... | 128/202.25 |
| 4,735,217 A | * | 4/1988 | Gerth et al. ................. | 131/273 |
| 4,973,047 A | * | 11/1990 | Norell ......................... | 482/13 |
| 4,993,436 A | * | 2/1991 | Bloom, Jr. .................. | 131/335 |
| 5,018,517 A | * | 5/1991 | Liardet ................... | 128/200.24 |
| 5,040,527 A | * | 8/1991 | Larson et al. .......... | 128/200.23 |
| 5,062,419 A | * | 11/1991 | Rider ..................... | 128/200.21 |
| 5,431,154 A | * | 7/1995 | Seigel et al. ........... | 128/200.14 |
| 5,443,059 A | * | 8/1995 | Koch et al. ............. | 128/200.16 |
| 5,451,190 A | * | 9/1995 | Liardet ........................ | 482/13 |
| 5,658,221 A | * | 8/1997 | Hougen ........................ | 482/13 |
| 5,720,282 A | * | 2/1998 | Wright ................... | 128/207.14 |
| 5,724,986 A | * | 3/1998 | Jones et al. ................. | 600/538 |
| 5,839,430 A | * | 11/1998 | Cama ..................... | 128/200.14 |
| 6,450,969 B1 | * | 9/2002 | Farr et al. ................... | 600/538 |
| 6,488,635 B1 | * | 12/2002 | Mottram ..................... | 600/551 |
| 6,500,095 B1 | * | 12/2002 | Hougen ........................ | 482/13 |

* cited by examiner

Primary Examiner—Aaron J. Lewis
(74) Attorney, Agent, or Firm—Edward P. Dutkiewicz

(57) ABSTRACT

A medication dosage inhaler system with a main body having a round hollow cylindrical inward portion and a plurality of apertures and a round hollow cylindrical inward portion with a radially displaced round cylindrical hollow medication passageway, a T-shaped adaptor having a stepped gas connector forming an open pathway for the deliverance of a medical gas, an end cap having a one way valve for a one way flow of gas there through and a plurality of apertures, a medication dosage delivery container having a projecting medication delivering tube, a mouthpiece, and an oxygen source to mate with the stepped gas connector of the T-shaped adaptor.

13 Claims, 6 Drawing Sheets

MEDICATION DOSAGE INHALER SYSTEM

BACKGROUND OF THE INVENTION

The present invention relates to a medication dosage inhaler system and more particularly pertains to allowing a patient to safely and efficiently deliver a predetermined medication dosage. Invention also provides breathing exercise, medical gas treatment, and nebulization therapy to the lungs of a patient.

Description of the Prior Art

The use of medication inhalers of known designs and configurations is known in the prior art. More specifically, medication inhalers and breathing exercisers of known designs and configurations previously devised and utilized for the purpose of administering medication dosages through conventional methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. Des. 280,765 to Alvino issued Sept. 24, 1985, discloses a design for respiratory muscle trainer. U.S. Pat. No. 4,533,137 to Sonne issued Aug. 6, 1985, discloses a pulmonary training method. Finally, U.S. Pat. No. 5,018,517 to Liardet issued May 28, 1991 discloses an expiration-resisting apparatus designed for improving pulmonary ventilation.

While these devices fulfill their respective, particular objectives and requirements, the aforementioned patents do not describe a medication dosage inhaler system that allows a patient to safely and efficiently deliver a predetermined medication dosage. Invention also provides breathing exercise, medical gas treatment, and nebulization therapy to the lungs of a patient.

In this respect, the medication dosage inhaler system according to the present invention substantially departs from the conventional concepts and designs of the prior art, and in doing so provides an apparatus primarily developed for the purpose of allowing a patient to safely and efficiently deliver a predetermined medication dosage, Invention also provides breathing exercise, medical gas treatment, and nebulization therapy to the lungs of a patient.

Therefore, it can be appreciated that there exists a continuing need for a new and improved medication dosage inhaler system which can be used for allowing a patient to safely and efficiently deliver a predetermined medication dosage. In this regard, the present invention substantially fulfills this need.

SUMMARY OF THE INVENTION

In view of the foregoing disadvantages inherent in the known types of medication inhalers of known designs and configurations now present in the prior art, the present invention provides an improved medication dosage inhaler system. As such, the general purpose of the present invention, which will be described subsequently in greater detail, is to provide a new and improved medication dosage inhaler system and method which has all the advantages of the prior art and none of the disadvantages.

To attain this, the present invention essentially comprises a cylindrical main body fabricated of rigid plastic material. The main body has an inward portion and an outward portion. The main body also has an inner surface and an outer surface with a radial edge 18 there between. The outward portion is formed in a round hollow cylindrical configuration with a first inside diameter and a first outside diameter and a wall thickness there between. The wall of the outward portion has an inward end and an outward end with a length there between. The outward end of the outward portion has a plurality of apertures there through. Each of the apertures has one of a plurality of internal diameters. The inward portion has a round hollow cylindrical configuration with a second inside diameter and a second outside diameter with a wall thickness there between. The second inside diameter is sized to receive and securely hold the first outside diameter of the outward portion. The inward portion has an inward end and an outward end. The inward portion also has a radially extending cylindrical hollow medication passageway located at the approximate midpoint between the inward end and the outward end. The passageway extends in an upward direction perpendicular to the primary axis of the main body. The passageway has a round inner surface and a round outer surface and a wall thickness there between. The inward portion of the main body is coupled to the outward portion of the main body at the outward end of the inward portion and the inward end of the outward portion. Next provided is a T-shaped adaptor. The T-shaped adaptor is fabricated of rigid plastic material in a round cylindrical hollow configuration. The adaptor has a second inside diameter and a second outside diameter and a wall thickness there between. The adaptor has a radially extending stepped gas connector located at the approximate midpoint of the adaptor. The connector forms an open pathway through the wall of the adaptor for the deliverance of a medical gas. An end cap is next provided. The end cap is fabricated of rigid material in a round hollow cylindrical configuration. The end cap has a second inner diameter and a second outer diameter with a wall thickness there between. The end cap has an inward end and an outward end and a length disposed there between. The outward end includes a one way valve with a plurality of cross members. The outward end also has a central point of attachment. The outward end also has a flexible flapper one way valve membrane located within the inner diameter to provide for a one way flow of gas through the end cap. The inward end has a plurality of apertures with each of the apertures having one of a plurality of diameters. The end cap apertures are located to be overlying the outward portion apertures of the main body when the end cap is coupled with the main body. When in position the end cap is rotatable for adjustment of air flow through the apertures. Next provided is a medication dosage delivery container. The container has a generally round delivery mouth and a round slightly tapered container portion. The delivery mouth has a projecting medication delivering tube. When positioned in the working configuration within the passageway of the inward portion, the tube lies in a radial axis to the primary axis at the approximate center of the primary axis of the inward portion. A mouthpiece is next provided. The mouthpiece is fabricated of rigid material. The mouthpiece has an outward portion and an inward portion. The outward portion is in a round cylindrical tubular configuration with a first inner diameter and a first outer diameter and is sized to be coupled with the inner portion of the main body. The inner portion of the mouthpiece is in a generally arcuate configuration to conform to a user's grip within the user's mouth. Finally, an oxygen source is provided. The oxygen source has a female adaptor configured to be received by and mate with the stepped gas connector of the T-shaped adaptor.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved medication dosage inhaler system which has all of the advantages of the prior art medication inhalers of known designs and configurations and none of the disadvantages.

It is another object of the present invention to provide a new and improved medication dosage inhaler system which may be easily and efficiently manufactured and marketed.

It is further an object of the present invention to provide a new and improved medication dosage inhaler system which is of durable and reliable constructions.

An even further object of the present invention is to provide a new and improved medication dosage inhaler system which is susceptible of a low cost of manufacture with regard to both materials and labor, and which accordingly is then susceptible of low prices of sale to the consuming public, thereby making such medication dosage inhaler system economically available to the buying public.

Even still another object of the present invention is to provide a medication dosage inhaler system for allowing a patient to safely and efficiently deliver a predetermined medication dosage.

Lastly, it is an object of the present invention to provide a new and improved medication dosage inhaler system with a main body having a round hollow cylindrical outward portion and a plurality of apertures and a round hollow cylindrical inward portion with a radially displaced round cylindrical hollow medication passageway, a T-shaped adaptor having a stepped gas connector forming an open pathway for the deliverance of a medical gas, an end cap having a one way valve for a one way flow of gas there through and a plurality of apertures, a medication dosage delivery container having a projecting medication delivering tube, a mouthpiece, and an oxygen source to mate with the stepped gas connector of the T-shaped adaptor.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
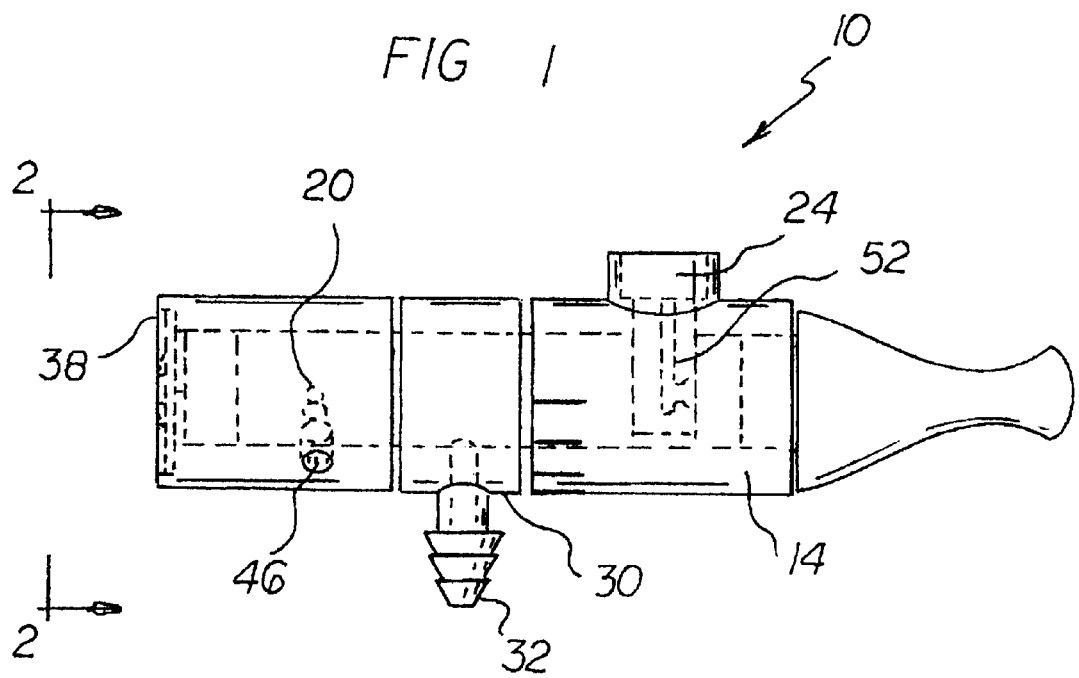
FIG. 1 is a side elevational view of the medication dosage inhaler system constructed in accordance with the principles of the present invention.
Figure 2:
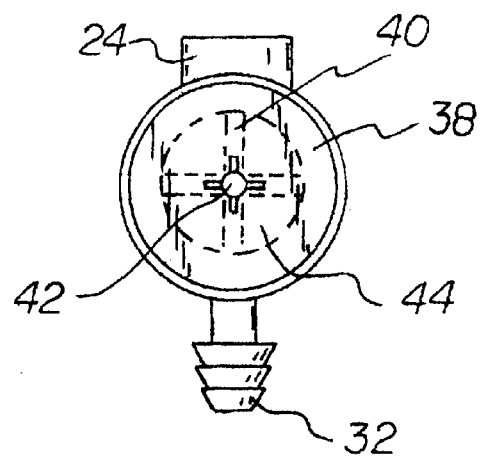
FIG. 2 is an end view of the system taken alone line 2—2 of FIG. 1.
Figure 3:
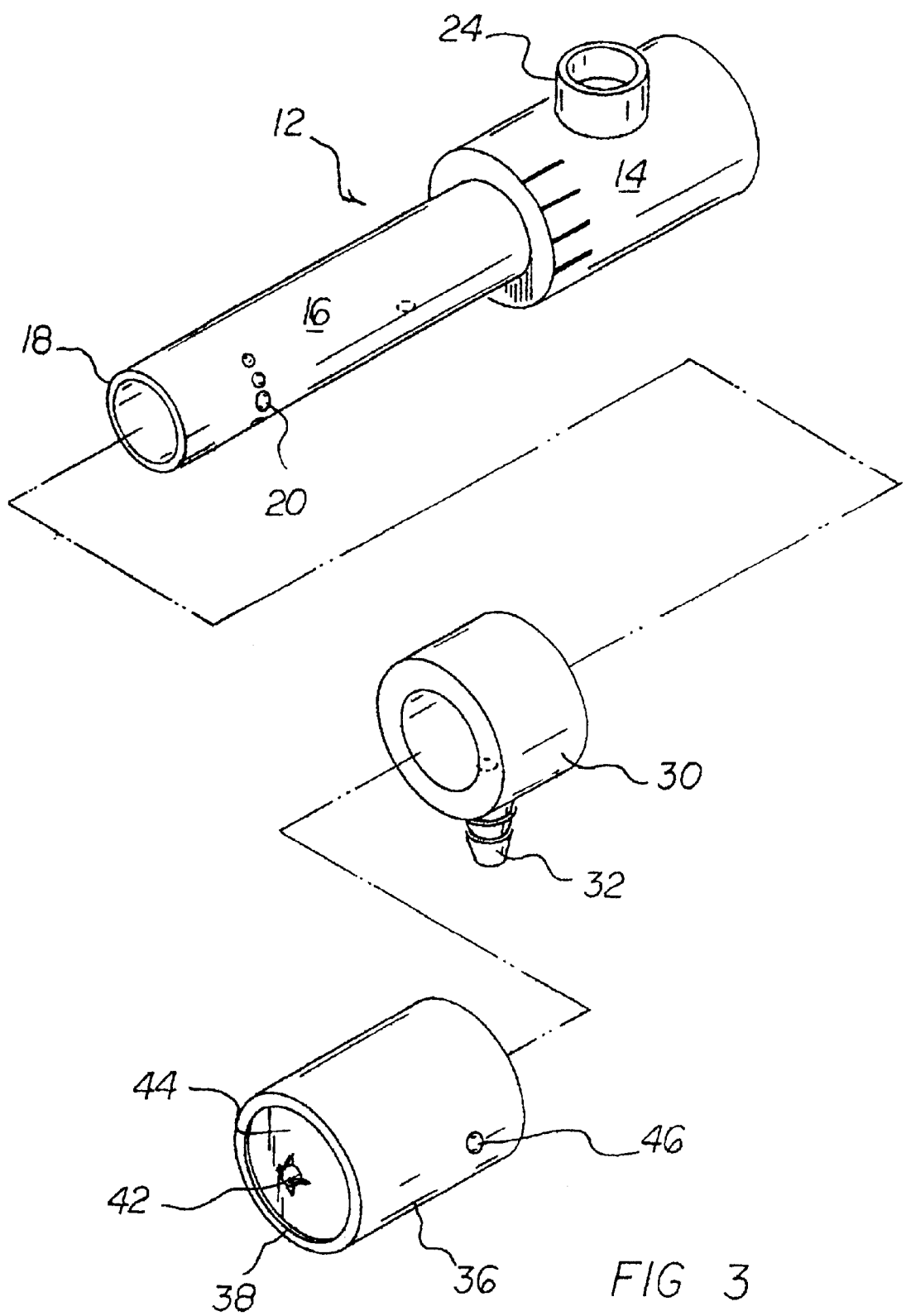
FIG. 3 is an exploded perspective view of the system shown in FIGS. 1 and 2.
Figure 4:
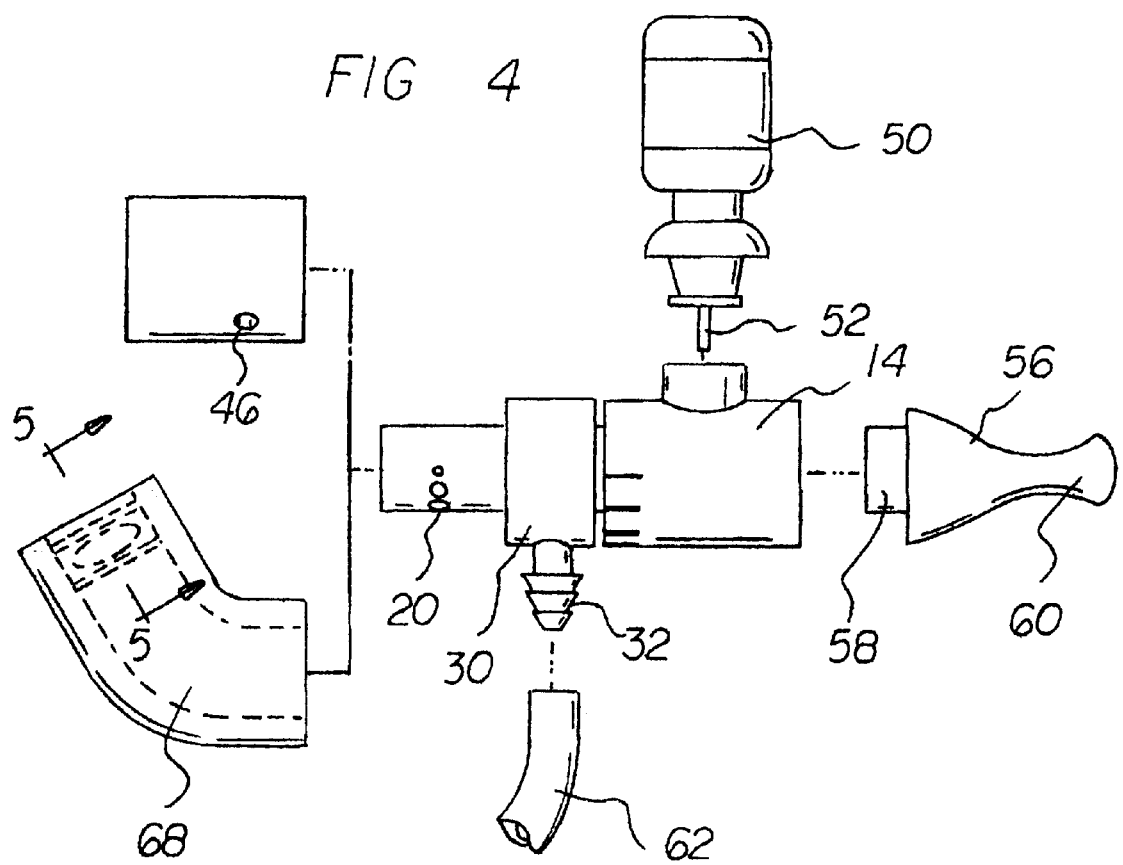
FIG. 4 is a side elevational view of the system shown in the prior Figures but with alternate end components.
Figure 5:
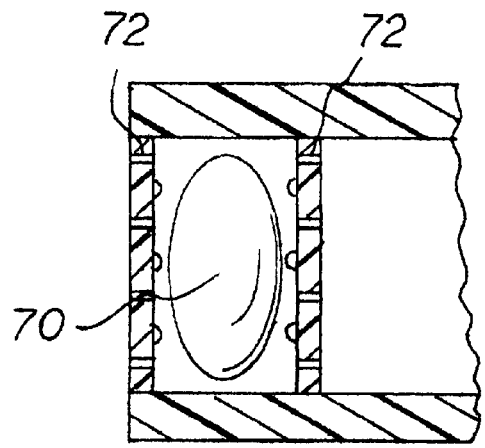
FIG. 5 is a cross sectional view taken along line 5—5 of FIG. 4.
Figure 6:
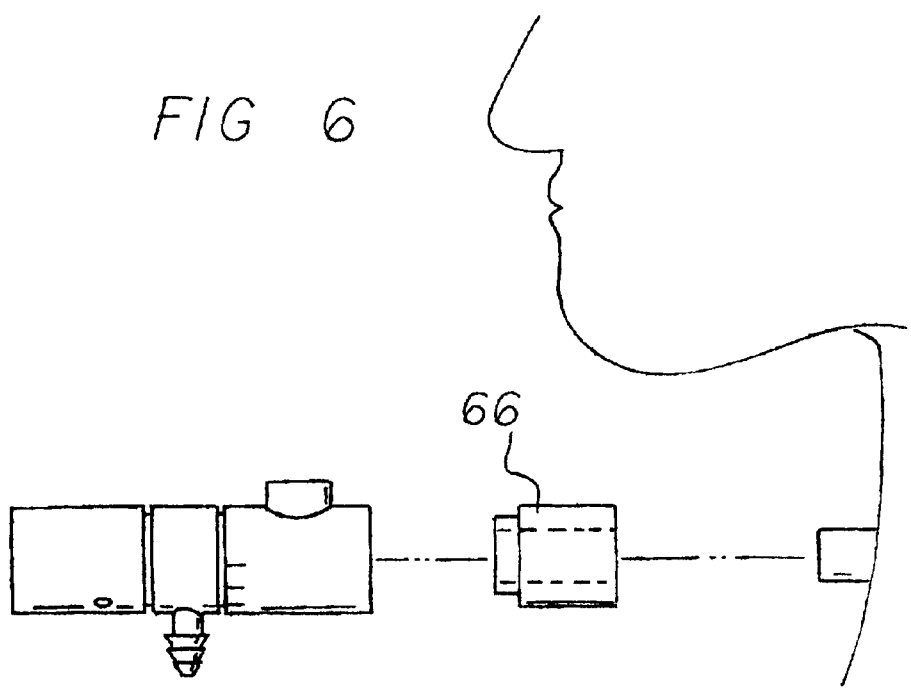
FIG. 6 is an exploded side elevational view of the system of the prior Figures modified for use in association with a tracheotomy.
Figure 7:
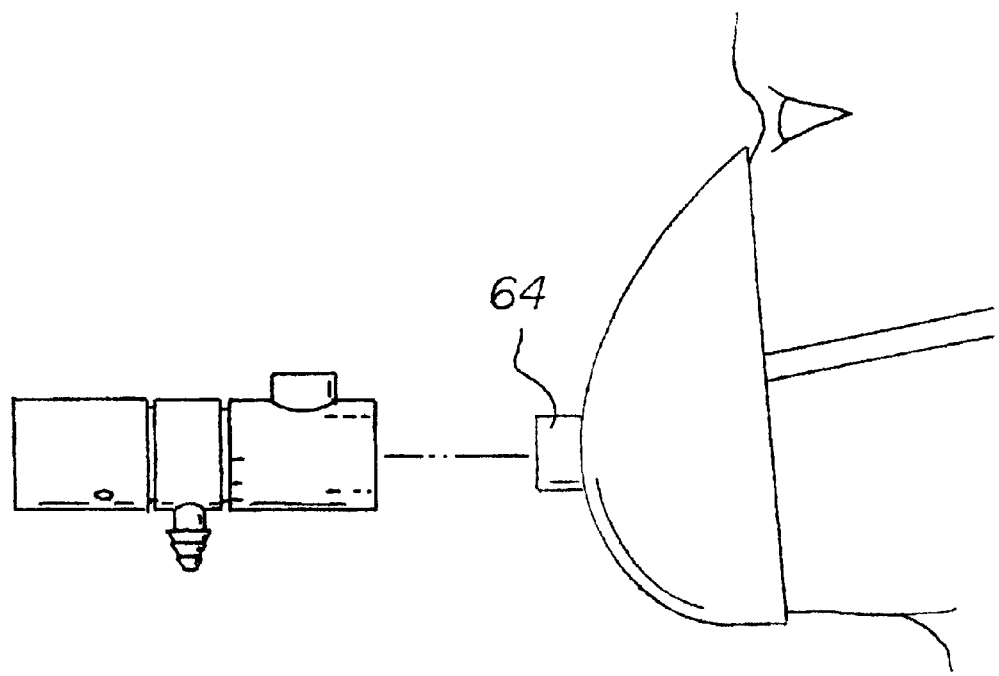
FIG. 7 is an exploded side elevational view similar to FIG. 6 but adapted for use in association with a mask.
Figure 8:
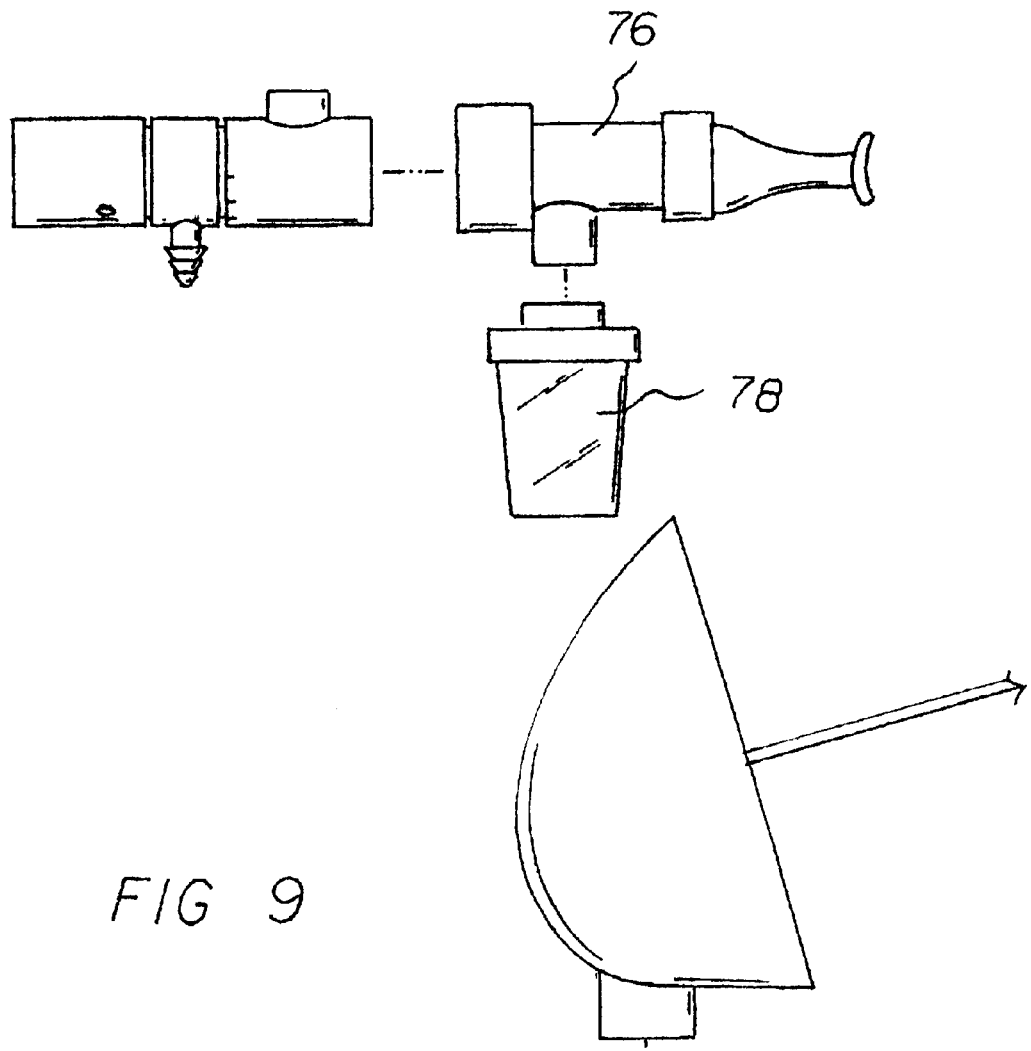
FIG. 8 is a device modified for breathing through the mouth modified to include a container of medication.
Figure 9:
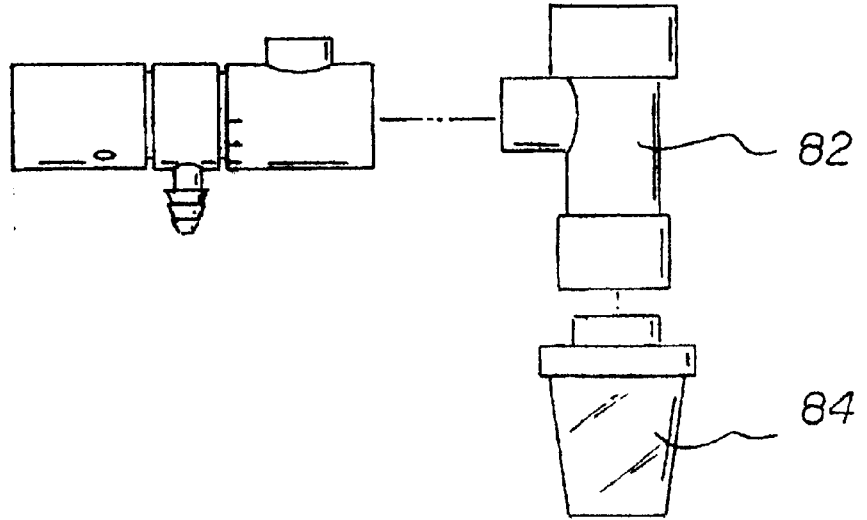
FIG. 9 is a view similar to FIG. 8 but modified for use in association with a mask.
Figure 10:
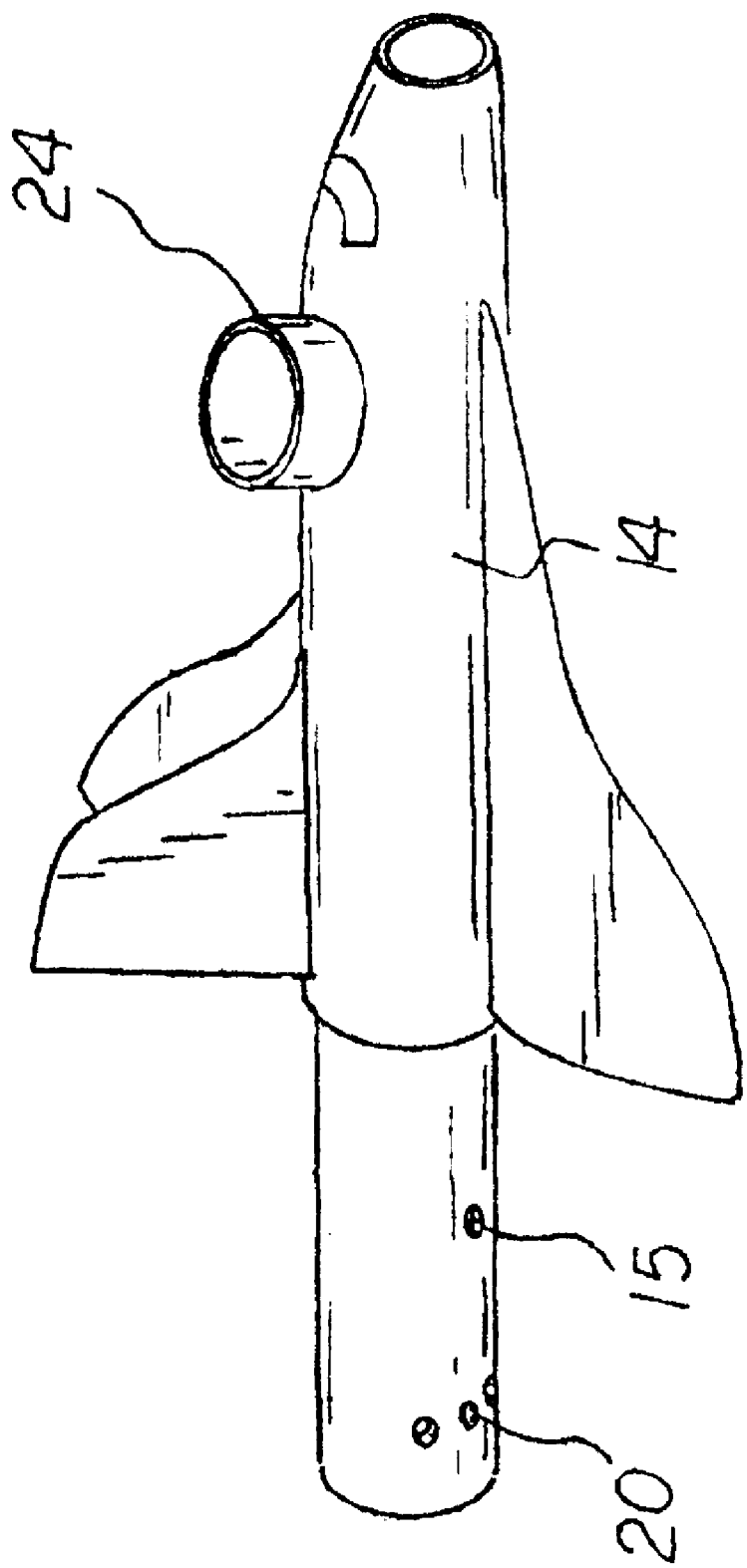
FIG. 10 is an alternate design of the invention, resembling a space shuttle, as an example of modifications that make the invention more marketable and desirable to pediatric patients.

With reference now to the drawings, and in particular to FIG. 1 thereof, the preferred embodiment of the new and improved medication dosage inhaler system embodying the principles and concepts of the present invention and generally designated by the reference numeral 10 will be described.

The present invention, the medication dosage inhaler system 10 is comprised of a plurality of components. Such components in their broadest context include a main body, a T-shaped adaptor, an end cap, a medication dosage delivery container, a mouthpiece, and an oxygen source. Such components are individually configured and correlated with respect to each other so as to attain the desired objective.

First provided is a cylindrical main body 12 fabricated of rigid plastic material. The main body has an inward portion 14 and an outward portion 16. The main body also has an inner surface and an outer surface with a radial edge 18 there between. The outward portion is formed in a round hollow cylindrical configuration with a first inside diameter and a first outside diameter and a wall thickness there between. The wall of the outward portion has an inward end and an outward end with a length there between. The outward end of the outward portion has a plurality of radially interior apertures 20 there through. Each of the apertures has one of a plurality of internal diameters. The inward portion 14 has a round hollow cylindrical configuration with a second inside diameter and a second outside diameter with a wall thickness there between. The second inside diameter is sized to receive and securely hold the first outside diameter of the outward portion. The inward portion has an inward end and an outward end. The inward portion also has a radially extending cylindrical hollow medication passageway 24 located at the approximate midpoint between the inward end and the outward end. The passageway extends in an upward direction perpendicular to the primary axis of the main body. The passageway has a round inner surface and a round outer surface and a wall thickness there between. The inward portion of the main body is coupled to the outward portion of the main body at the outward end of the inward portion and the inward end of the outward portion.

Next provided is a T-shaped adaptor 30. The T-shaped adaptor is fabricated of rigid plastic material in a round cylindrical hollow configuration. The adaptor has a second inside diameter and a second outside diameter and a wall thickness there between. The adaptor has a radially extending stepped gas connector 32 located at the approximate midpoint of the adaptor. The connector forms an open pathway through the wall of the adaptor, and through aperture 15 of the outward portion 16 of the main body, for the deliverance of a medical gas. Adaptor is rotatable when coupled to the outward portion of the main body, to allow gas to enter the main body when connector is aligned with aperture 15. Aperture 15 is sealed when adaptor is rotated so that its connector is not aligned with aperture 15, thereby blocking the passage of gas.

An end cap 36 is next provided. The end cap is fabricated of rigid material in a round hollow cylindrical configuration. The end cap has a second inner diameter and a second outer diameter with a wall thickness there between. The end cap has an inward end and an outward end and a length disposed there between. The outward end includes a one way valve 38 with a plurality of cross members 40. The outward end also has a central point of attachment 42. The outward end also has a flexible flapper one way valve membrane 44 located within the inner diameter to provide for a one way flow of gas through the end cap. The inward end has a plurality of radially exterior apertures 46 with each of the apertures having one of a plurality of diameters. The end cap apertures are located to be overlying the outward portion apertures of the main body when the end cap is coupled with the main body. When in position the end cap is rotatable for adjustment of air flow through the apertures.

Next provided is a medication dosage delivery container 50. The container has a generally round delivery mouth and a round slightly tapered container portion. The delivery mouth has a projecting medication delivering tube 52. When positioned in the working configuration within the passageway of the inward portion, the tube lies in a radial axis to the primary axis at the approximate center of the primary axis of the inward portion.

A mouthpiece 56 is next provided. The mouthpiece is fabricated of rigid material. The mouthpiece has an outward portion and an inward portion. The outward portion is in a round cylindrical tubular configuration 58 with a first inner diameter and a first outer diameter and is sized to be coupled with the inner portion of the main body. The inner portion of the mouthpiece is in a generally arcuate configuration 60 to conform to a user's grip within the user's mouth.

Finally, an oxygen source 62 is provided. The oxygen source has a female adaptor configured to be received by and mate with the stepped gas connector of the T-shaped adaptor.

The long, internal spacer region of the main body serves as a reserve chamber for aerosol and/or nebulized medication or therapies.

In an alternate embodiment of the invention, a mask adaptor 64 is provided. The mask adaptor is in a generally round and hollow cylindrical configuration. The mask adaptor has an inward end and an outward end-and a length disposed there between. The adaptor has a first inner diameter and a first outer diameter and is sized to be received by and firmly held by the main body of the system. The inner end of the adaptor is coupleable to a face mask. In this manner the face mask is utilized to provide a medication being delivered by the system.

In another alternate embodiment of the system, a tracheotomy adaptor 66 is provided. The tracheotomy adaptor has a generally round, hollow cylindrical configuration. The tracheotomy adaptor has an inward end and an outward end and a length disposed there between. The adaptor has a first inner diameter and a first outer diameter and is sized to be received by and firmly held by the main body of the system. The inner end has an inner diameter sized to receive and be firmly mated with a tracheotomy tube.

In still another embodiment of the system, an angled end cap 68 is provided. The angled end cap is fabricated of rigid material in a round hollow cylindrical configuration. The angled end cap has a second inner diameter and a second outer diameter with a wall thickness there between. The end cap also has an inward end and an outward end and a length disposed there between. The outward end has a one-way elastomeric exhaust ball valve 70. A plurality of cross members 72 contain the ball valve within the inner diameter to provide for a one-way flow of gas through the end cap. The ball is loosely held between cross members 72, so that the ball rattles inside its chamber as exhaled air passes through end cap 68. The rattling of the ball causes the flow of exhaled air to be vibrational, pulsating, and semi-discontinuous.

In yet another embodiment of the system, an optional T-shaped piece 76 is provided. The optional T-shaped piece is coupleable between the body and the adaptor with a downwardly extending leg and a medication container 78, a nebulizer, coupled to the leg.

In a final embodiment of the invention, an additional optional T-shaped piece 82 is provided. The additional optional T-shaped piece is coupleable between a mask and the body and a medication container 84, a nebulizer, is coupleable to the additional optional T-shaped piece.

In view of the foregoing disadvantages and limitations inherent in the known types of breathing exercisers and inhalers of known designs and configurations now present in the prior art the present invention provides an improved inspiratory exerciser and universal therapy delivery system adapted to fit oxygen tubing, masks, nebulizers, and tracheotomies, including an optional port to accept and dispense a canister of metered dosage medication.

To attain this, the present invention essentially comprises a main body. The main body has an oblong, cylindrical configuration, that also serves as a spacer region and reserve chamber. The front portion has a cylindrical protruding user adaptor portion that continues from the main body. The rear cylindrical end includes an elastomeric exhaust valve 38 fabricated of a soft resilient elastomeric material. The exhaust valve is adapted to allow the exhaling of air to exterior of the body by a patient independent of the pressure of exhaling. In an intermediate region between the front and rear cylindrical ends exists a rotating user dial, or rotating or sliding sheath, for controlling air resistance with different settings. The main body contains several apertures or, in an alternate embodiment, a single large aperture in this region. The purpose of such aperture or apertures is to provide entry of external air into the system. Air will then traverse through the device and out the front cylindrical end to read the user's respiratory tract. The aperture or apertures can be gradually covered or exposed by turning or sliding the user dial or sheath. Air intake resistance decreases as the area of exposed aperture or apertures increases. The end cap 36, a dial or sheath, which covers the radially interior apertures 20 in the main mower, itself has a radially exterior aperture or apertures 46. When the apertures or apertures of the end cap are aligned with some or all of the aperture or apertures of the main body, external air is allowed to enter the system. When some aperture or apertures in the dial are not aligned with aperture or apertures of the main mower, those apertures do not allow air to enter the system. The end cap may either rotate around the main axis of the mower or around an axis that is perpendicular to the main axis. Alternatively, a sliding sheath, not shown, with or without holes, may cover or expose apertures in the main body. Indicia are provided on or near the user controlled air resistance end cap so that inhalation resistance, preferably flow rate in units of cubic centimeters per second, is clearly marked. Such indicia allow said invention to serve as a measuring device to approximately determine volume of inhalation capacity when the duration of inhalation is timed.

An optional port, or passageway 24, to accept, support, and dispense a canister of metered dosage medication may reside on the top surface of the main mower. This port is designed to be universal in its acceptance of medication canisters. A circular lip may surround this port to better support the medicine canister. The port includes a downwardly extending nozzle extending through this port and into the main mower. Depressing the canister will dispense a pre-metered dosage of a medicine into the mower for being inhaled by a patient.

The main body fits a T-shaped oxygen-tubing adaptor 30. This adaptor may be free to rotate clockwise or counter-clockwise around the main axis of the mower, thereby opening or closing a hole 15 in the main mower, so that a path out to the oxygen tubing is established. Therefore, the user may be able to seal the oxygen-tubing adaptor from the main mower when oxygen tubing is not connected. Alternatively, this T-shaped oxygen-tubing adaptor can be incorporated as a component in the main mower.

The front cylindrical end of the main mower, or after the T-shaped oxygen-tubing adaptor, is designed to fit several other adaptors.

One such adaptor is a T-shaped nebulizer adaptor. Nebulizers are currently used with this same T-shaped adaptor and mouthpiece. The body of this T-shaped adaptor has a downward facing aperture with a neck that fits a nebulizer, or supplemental medication container. The inward or proximal end of this adaptor fits a mouthpiece. In the past, the outward or distal end of this adaptor has been left open so that a great deal of nebulized medication is lost to the atmosphere. Also in the past, a long tube has been attached to the distal end of this adaptor to partially reduce the nebulized medication lost to the atmosphere. These past methods are highly inefficient and wasteful. By attaching the current invention to the distal end of this T-shaped nebulizer adaptor, a closed system is created so that very little medication is lost to the atmosphere. The other benefit of using said invention in conjunction with a nebulizer is to allow nebulized medication to be taken much deeper into the lungs using the patient's positive pressure created by the inhalation resistance established by the invention.

This invention can be attached to a mask or tracheotomy, either directly, or with a tubing adaptor. This tubing may be flexible or rigid. Patients who are too weak to hold the system of the present invention, can utilize the device hands free when the device is attached to a mask. The mask has an elastic band that holds the mask on the head. Masks are form fitted to the face and make a seal. The mask has a proximal outlet port to which the invention or tubing adaptor can be attached. Masks are very beneficial for patients suffering from pulmonary edema. In such cases, nebulized alcohol solutions are required. This invention attached to a nebulizer with a T-shaped adaptor and attached to the mask would greatly satisfy this need. A mask utilized with the present invention is also beneficial for infants and the elderly in receiving nebulization therapy and/or oxygen treatments. A mask can also be form fitted to a dog or other animal, allowing invention to be used in veterinary care.

This invention can also be used on patients with a tracheotomy. This allows the delivery of nebulized medication, metered dosage medication, and oxygen treatments to these patients. Importantly, this invention also provides inhalation exercise to the lungs and diaphragm of patients with a tracheotomy. This exercise can help in rehabilitating these patients and in weaning these patients from a ventilator.

The other type of adaptor that fits the present invention is a mouthpiece, similar to those used with a nebulizer.

The present invention is also a therapeutic device to treat victims of acts of terrorism by serving as a drug delivery device to administer exercise and medicines and/or therapies to the respiratory tract of individuals suffering from respiratory illnesses. This device can, therefore, provide therapy to individuals suffering from biological terrorism or from inhalation of dust, debris, smoke, and other harmful substances associated with fires and collapsed buildings. Therefore, the need to have this product patented and produced is of utmost importance and a matter of urgency given our nation's current situation.

Some alternative embodiments of the invention consist of a long-internal spacer region with a face that includes a user controlled air resistance end cap with supplemental apertures. This end cap is rotatable for controlling the amount of additional air allowed to enter through apertures associated with the end cap, thus regulating inhalation resistance. The top face further includes a flush circular medication adaptor. The medication adaptor has a small aperture passing there through with a circular lip extending outwardly for supporting a container within the small aperture.

A one-way valve, whose material is impermeable to air, would open to allow expired air to exit the internal chamber of the device, and close to prevent inhaled air from entering.

Alternatively, a one-way valve whose material is semi-permeable to air, would open to allow expired air to exit the internal chamber of the device, and close to prevent the bulk of inhaled air from entering, yet would allow some flow of air to penetrate its material into the internal chamber of the device.

Some embodiments of the device are streamlined to produce a much smaller unit, requiring less material and assembly in its construction. The production, packaging, and shipping of such embodiment can be less expensive. Because of its smaller size and less cost, this embodiment can be marketed to be disposable after a designated period of time. Also, such a smaller unit may be desirable for certain application.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the united states is as follows:

1. A medication dosage inhaler system for allowing a patient to safely and efficiently deliver a predetermined medication dosage comprising, in combination:

a cylindrical main body fabricated of rigid plastic material having an inward portion and an outward portion with an inner surface and an outer surface with a radial edge there between, the outward portion having a round hollow cylindrical configuration with a first inside diameter and a first outside diameter and a wall thickness there between with the outward wall of the outward portion having an inward end and an outward end with a length there between, the outward end of the outward portion having a plurality of apertures there through with each of the apertures having one of a plurality of internal diameters, the inward portion having a round hollow cylindrical configuration with a second inside diameter, sized to receive and securely hold the first outside diameter of the outward portion and a second outside diameter and a wall thickness there between with the inward portion having an inward end and an outward end, with the inward portion having a radially extending cylindrical hollow medication passageway located at the approximate midpoint between the inward end and the outward end with the passageway extending in an upward direction and perpendicular to the primary axis of the main body, the passageway having a round inner surface and a round outer surface and a wall thickness there between, with the inward portion of the main body being coupled to the outward portion of the main body at the outward end of the inward portion and the inward end of the outward portion;

a T-shaped adaptor fabricated of rigid plastic material and having round cylindrical hollow configuration with a second inside diameter and a second outside diameter and a wall thickness there between with the adaptor having a radially extending stepped gas connector located at the approximate midpoint of the adaptor, the connector forming an open pathway through the wall of the adaptor for the deliverance of a medical gas, the adaptor can be rotatable so that the passage of gas can be opened or sealed with respect to alignment with an aperture in the main body;

an end cap fabricated of rigid material and having a round hollow cylindrical configuration with a second inner diameter and a second outer diameter with a wall thickness there between with the end cap having an inward end and an outward end and a length disposed there between with the outward end including a one way valve with a plurality of cross members, a central point of attachment and a flexible flapper one way valve membrane located within the inner diameter to provide for a one way flow of gas through the end cap and the inward end having a plurality of apertures with each of the apertures having one of a plurality of diameters with the end cap apertures being located to be overlying the outward portion apertures of the main body when the end cap is coupled with the main body and when in position the end cap being rotatable for adjustment of air flow through the apertures, and thus controlling inhalation resistance;

a medication dosage delivery container having a generally round delivery mouth and a round slightly tapered container portion with the delivery mouth having a projecting medication delivering tube which, when positioned in the working configuration within the passageway of the inward portion lies in a radial axis to the primary axis at the approximate center of the primary axis of the inward portion;

a mouthpiece fabricated of rigid material having an outward portion and an inward portion, the outward portion having a round cylindrical tubular configuration with a first inner diameter and a first outer diameter and sized to be coupled with the inner portion of the main body, with the inner portion of the mouthpiece having a generally arcuate configuration to conform to the user's grip within the user's mouth; and an oxygen source having a female adaptor configured to be received by and mate with the stepped gas connector of the T-shaped adaptor.

2. A medication dosage inhaler system comprising, in combination:

a main body having an inward portion and an outward portion, the outward portion having a round hollow cylindrical configuration and having a plurality of apertures there through, the inward portion having a round hollow cylindrical configuration with a radially displaced round cylindrical hollow medication passageway;

a T-shaped adaptor having a stepped gas connector forming an open pathway for the deliverance of a medical gas, the adaptor being rotatable so that the passage of gas can be opened or sealed with respect to alignment with an aperture in the main body;

an end cap having a one way valve for a one way flow of gas there through and a plurality of apertures;

a medication dosage delivery container having a projecting medication delivering tube;

a mouthpiece; and an oxygen source to mate with the stepped gas connector of the T-shaped adaptor.

3. A medical dosage inhaler system as described in claim 2 wherein the system further comprises:

a long, internal spacer region of the main body which serves as a reserve chamber for aerosol and nebulized medication and therapies.

4. A medical dosage inhaler system as described in claim 2 wherein the system further comprises:

adjustable inhalation resistance settings to provide breathing exercise to the lungs and diaphragm of a patient whereby inhalation resistance allows the patient to create his own positive pressure that sends metered-dosage medication, medical gas and nebulized medicine and therapies much deeper into the lungs via a forced stream of inhaled air so that more medicine reaches its target deep down into the lungs, and less medicine is lost and wasted along the way whereby resistance settings can be labeled with calibrating indicia on the surface of invention.

5. A medication dosage inhaler system as described in claim 2 wherein the system further comprises:

a mask adaptor having a generally round, hollow cylindrical configuration with an inward end and an outward end and a length disposed there between with the adaptor having a first inner diameter and a first outer diameter and sized to be received by and firmly held by the main body of the system and with the inner end of the adaptor being coupleable to a face mask for the utilization of the face mask to provide a medication being delivered by the system.

6. A medication dosage inhaler system as described in claim 2 wherein the system further comprises;

a tracheotomy adaptor having a generally round, hollow cylindrical configuration with an inward end and an outward end and a length disposed there between with the adaptor having a first inner diameter and a first outer diameter and sized to be received by and firmly held,by the main body of the system and with the inner end having an inner diameter sized to receive and be firmly mated with a tracheotomy tube.

7. A medication dosage inhaler system as described in claim 2 wherein the system further comprises:

an angled end cap fabricated of rigid material and having a round hollow cylindrical configuration with a second inner diameter and a second outer diameter with a wall thickness there between with the end cap having an inward end and an outward end and a length disposed there between with the outward end having a one way ball valve having a plurality of cross members to contain the ball valve within the inner diameter to provide for a one way flow of gas through the end cap, the ball being loosely held between cross members, so that the ball rattles inside its chamber as exhaled air passes through this type of end cap, rattling of the ball causing the flow of exhaled air from the patient to be vibrational, pulsating, and semi-discontinuous, vibrational motion of the patient's exhaled air, and the vibrational movement of the patient's lungs, tending to break up and dislodge mucous along the patient's respiratory tract, causing the mucous to be easier to clear from the respiratory tract.

8. A medication dosage inhaler system as described in claim 2 wherein the system further comprises:

an optional T-shaped piece coupleable between the body and the adaptor with a downwardly extending leg and a medication container coupled to the leg, this configuration providing a more closed system that helps prevent nebulized medication from being lost to the atmosphere, as would occur if the nebulizer and T-shaped piece were used without this invention, as in the past, nebulized medication and therapies are used more efficiently with this invention, and taken deeper into the lungs using the patient's positive pressure of inhalation.

9. A medical dosage inhaler system as described in claim 2 wherein the system further comprises:

an additional optional T-shaped piece coupleable between a mask and the body and a medication container coupleable to the additional optional T-shaped piece, this configuration allowing for use on infants, incapacitated and elderly patients to provide breathing exercise, metered-dosage medication, medical gas, and nebulization therapy to the lungs of these patients.

10. A medical dosage inhaler system as described in claim 2 wherein the system further comprises:

a mask form fitted to a dog or other animal so that invention can be used to deliver breathing exercise, metered-dosage medication, medical gas, and/or nebulization therapy to veterinary patients.

11. A medical dosage inhaler system as described in claim 2 wherein the system further comprises:

a mask form fitted to a dog or other animal so that system can be used to deliver breathing exercise, metered-dosage medication, medical gas, and nebulization therapy to veterinary patients.

12. A medical dosage inhaler system as described in claim 7 wherein the system further comprises at least of the following:

a shape that resembles an object, such as an aircraft and space shuttle that is appealing to children, the system being comprised of fluorescent material to glow in the dark, caricatures being displayed on the system, apertures being provided to produce a desirable sound or music upon inhalation and exhalation, thereby increasing the marketability of the system to pediatric patients, and enhance the desirability and utilization of the system by children.

13. A medical dosage inhaler system as described in claim 2 wherein the system provides for the simultaneous use at least one of the following treatments: breathing and inhalation exercise, metered-dosage medication or therapies, nebulized medication or therapies, oxygen and medical gas delivery, and vibrational exhalation therapy to loosen mucous in the respiratory tract.

* * * * *